United States Patent [19]

Sentoku et al.

[11] 3,995,055
[45] Nov. 30, 1976

[54] METHOD FOR TREATING PEPTIC ULCERS

[75] Inventors: Mitsuhiko Sentoku; Hiroshi Fujita; Shunzo Aibara, all of Tokyo, Japan

[73] Assignee: Daiichi Seiyaku Co., Ltd., Tokyo, Japan

[22] Filed: Feb. 28, 1975

[21] Appl. No.: 554,042

[52] U.S. Cl. ............................................. 424/309
[51] Int. Cl.² ........................................ A61K 31/24
[58] Field of Search ................................. 424/309

[56] References Cited
UNITED STATES PATENTS 3,793,292   2/1974   Yamamura et al. ............. 424/309

*Primary Examiner*—Frederick E. Waddell
*Attorney, Agent, or Firm*—Sughrue, Rothwell, Mion, Zinn & Macpeak

[57] ABSTRACT

A method for treating peptic ulcers comprising administering a therapeutically effective amount of a compound of the general formula (I)

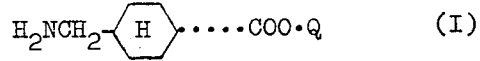

(I)

wherein Q is an unsubstituted or substituted phenyl or β-naphthyl group, the substituted phenyl group being selected from the group consisting of a p-halophenyl group, an o-alkoxy-p-formylphenyl group, a diphenyl group, a p-carboxyvinylphenyl group, a p-carboxyphenyl group, a p-(β-aminocarboxyethyl)phenyl group and a p-carboxy lower alkyl-phenyl group, or a pharmaceutical composition containing a therapeutically effective amount of a compound of the general formula (I) as an active ingredient to a patient afflicted therewith.

6 Claims, 4 Drawing Figures

METHOD FOR TREATING PEPTIC ULCERS

BACKGROUND OF THE INVENTION

1. Field of the Invention

This invention relates to an agent for and a method for treating peptic ulcers.

2. Description of the Prior Art

Various investigations on the causes of and therapy for peptic ulcers have led to the conclusion that there is no single cause of peptic ulcers, but a number of factors participate in the cause. It is, however, generally accepted that peptic ulcers are caused mainly by two important factors, one factor (the so called "aggressive factors") being typically exemplified by a volume and acid concentration of gastric juice (acid, pepsin, volume, etc.) and the other factor (the so called "defensive factors") being the reduction of the defensive capability of the mucous membranes of the stomach and adjoining digestive tract, typically shown by the metabolism of the gastric mucous membrane. In other words, the cause of peptic ulcers is considered to lie in an unbalance between the aggressive factors and the defensive factors. Accordingly, various therapeutic agents for treating peptic ulcers have previously been developed and used appropriately depending on the causes of the peptic ulcers.

Conventional treating agents for peptic ulcers can be classified as follows depending on the causes of peptic ulcers.

1. Inhibitor type agents against aggressive factors: Anti-acids (e.g., sodium bicarbonate, aluminum compounds), Anti-pepsin agents (e.g., aluminum sucrose sulfate), Anticholinergic agents (e.g., atropin sulfate).
2. Promotor type agents for defensive factors: Agents for protecting, or promoting the regeneration of, the mucous membranes (e.g., gefarnate, glutamine, vitamin U, aluminum sucrose sulfate).

Therapeutic agents acting simultaneously on the above two important factors, aggressive and defensive, are ideal in the therapy of peptic ulcers, but the only agents of this kind available at present are aluminum sucrose sulfate and inorganic aluminum salts. However, aluminum sucrose sulfate has a strong characteristic as a mucosa-protecting agent, and inorganic aluminum salts do not exhibit a definite mucosa-protecting activity. It has, therefore, been intensively desired to develop therapeutic agents which will act strongly on these two factors.

SUMMARY OF THE INVENTION

From this viewpoint, extensive studies on useful therapeutic agents for peptic ulcers have been made and it has been found that compounds represented by the general formula (I) exhibit very superior treating effects on peptic ulcers.

Accordingly, an object of this invention is to provide a superior therapeutic agent for peptic ulcers.

Another object of this invention is to provide a method for treating peptic ulcers using the above new therapeutic agent.

Further, an object of this invention is to provide a method for treating peptic ulcers comprising administering a therapeutically effective amount of an amino acid ester of the general formula (I)

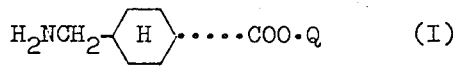

wherein Q is an unsubstituted or substituted phenyl or β-naphthyl group, the substituted phenyl group being selected from the group consisting of a p-halophenyl group, an o-alkoxy-p-formylphenyl group, a diphenyl group, a p-carboxyvinylphenyl group, a p-carboxyphenyl group, a p-(β-aminocarboxyethyl)phenyl group and a p-carboxy-lower alkyl-phenyl group, to a patient afflicted therewith.

DETAILED DESCRIPTION OF THE INVENTION

Figure 1:
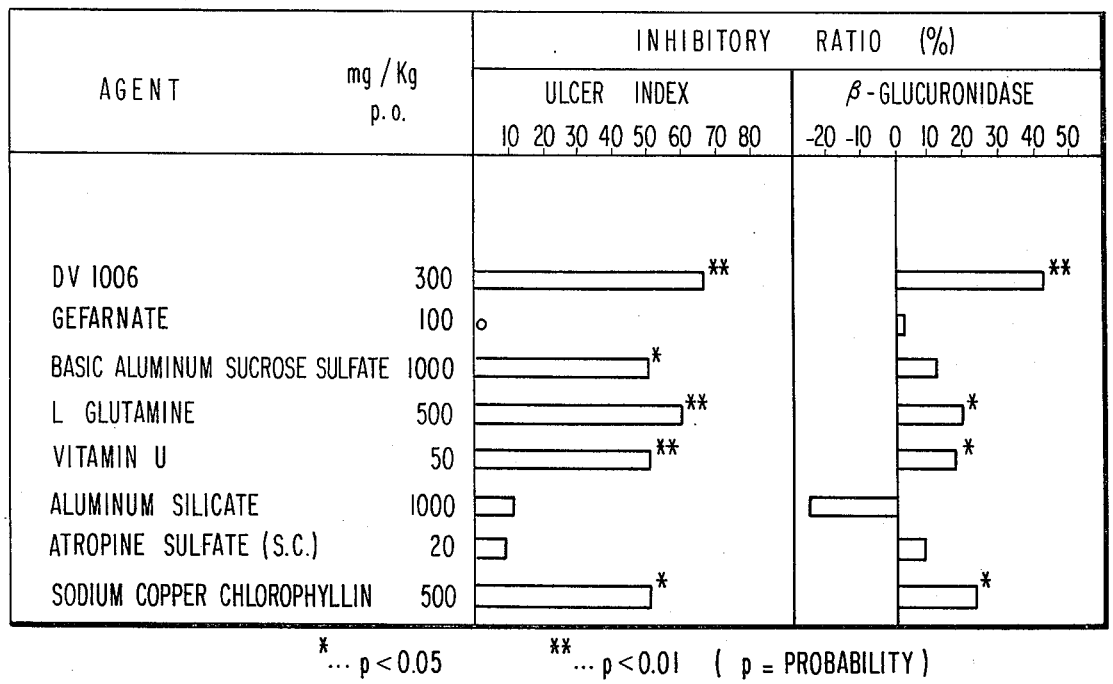
FIG. 1 shows the effect of 4'-(2-carboxyethyl)-phenyl.trans-4-aminomethylcyclohexane carboxylate and various known comparative ulcer treating agents with respect to the ulcer index and β-glucuronidase activity in glandular stomach tissue of rats with acetic ulcers (10% acetic acid) 9 days after operation as described in the examples.

As a result of examining the curing effects of the therapeutic agent of this invention on various ulcer models, it has been confirmed that the compounds of formula (I) of this invention exhibit superior effects both on the aggressive factors and on the defensive factors in the treatment of peptic ulcers. Specifically, examination was made of (A) the curing effects on Shay ulcers (an ulcer model mainly strengthening the aggressive factors), and (B) the curing effects on drug ulcers, clamping ulcers, clamping-cortisone ulcers and acetic ulcers (ulcer models mainly reducing the defensive factors).

In the above studies and clinical tests on the various ulcer models, 4'-(2-carboxyethyl)phenyl.trans-4-aminomethylcyclohexane carboxylate (hereinafter referred to as DV-1006), which is a compound of formula (I) wherein Q is a p-carboxyethylphenyl group, was used as a representative example of the compounds of formula (I). The significance of the curing effects of the other compounds of formula (I) on Shay ulcers was determined statistically in a similar manner to the case of DV-1006. As compared with the results of DV-1006, it was acertained that the remaining compounds of the formula (I) were also effective for the treatment of peptic ulcers.

In the evaluation of new therapeutic agents for peptic ulcers, the above-mentioned test method is usually employed at present to determine those factors upon which a specific treating agent would act, or to determine the strength with which the agent would act. The results obtained in DV-1006 are summarized below.

I. Examination of the Usefulness as Anti-Ulcer Agent:

a. Determination of factors on which DV-1006 acts:

As shown in the following table, DV-1006 simultaneously acts both on aggressive and defensive factors.

Table 1

|  | DV-1006 | Conventional Anti-ulcer Agent | | | |
|---|---|---|---|---|---|
|  |  | Anti-acid Type (aluminum silicate) | Anti-pepsin Agent Type (aluminum sucrose sulfate) | Anticholinergic Agent Type (atropine sulfate) | Mucosa-Protecting and Regenerating Agent Type (gefarnate) |
| Aggressive Factors |  |  |  |  |  |
| Shay Ulcer | + | + | + | + | − |
| Defensive Factors |  |  |  |  |  |
| Drug Ulcer | + | + | + | − | + |
| Clamping-Cortisone Ulcer | + | − | − | − | + |
| Clamping Ulcer | + | + | + | − | + |
| Acetic Ulcer | + | − | + | + | − |

Note: + = Effectiveness
− = No effectiveness b. Degree of Effect:

The degree of effect of DV-1006 was compared with those of conventional anti-ulcer agents, and the results obtained are tabulated in Table 2 below.

Table 2

| Ulcer Model | Order of the Strength of Action | | |
|---|---|---|---|
|  | First | Second | Third |
| Shay Ulcer | DV-1006 | Gefarnate | — |
| Drug Ulcer | DV-1006 | Gefarnate | Aluminum sucrose sulfate |
| Clamping-Cortisone Ulcer | DV-1006 | Gefarnate | Aluminum sucrose sulfate |
| Clamping Ulcer | Aluminum Silicate | Gefarnate | DV-1006 |
| Acetic Ulcer | DV-1006 | Gefarnate | Aluminum sucrose sulfate |

It is noted from the above that DV-1006 exhibits an especially strong action on acetic ulcers and clamping-cortisone ulcers which are models of chronic ulcers.

II. Examination of the Mode of Activity:

As stated above, DV-1006 acts very strongly both on the aggressive factors and the defensive factors as compared with conventional anti-ulcer agents. It was also found that DV-1006 has a superior action on gastric juice not observed with conventional anti-ulcer agents. In the treatment of peptic ulcers, the action of an agent on the gastric juice can be classified roughly into the following five categories:

1. An inhibitory action on the activity of pepsin itself,
2. An inhibitory action on the secretion of pepsin,
3. An inhibitory action on acids,
4. An inhibitory action on the secretion of acids, and
5. An activity of controlling gastric juice.

Therapeutic agents having the activity classified in category (2) above are especially desired.

Heretofore, anti-pepsin agents and anti-acids are representative of anti-ulcer agents relating to gastric juice, and anticholinergic agents have also been considered as effective in this area. However, anti-pepsin agents act only as category (1) above, and anti-acids act only as category (3). Anitcholinergic agents are considered to act as categories (4) and (5), but these have not yet been confirmed definitely as category (2).

This relation is shown in Table 3 below in which the symbol (+) shows that a particular agent has the indicated activity, whereas the symbol (−) shows that the particular agent does not have the indicated activity and symbol (±) shows that the particular agent has a slight activity.

Table 3

| Action on Gastric Juice | DV-1006 | Anti-pepsin Agent | Anti-acid | Anticholinergic Agent |
|---|---|---|---|---|
| Pepsin Activity | − | + | − | − |
| Pepsin Secretion | + | − | − | ± |
| Acids Activity | − | − | + | − |
| Acid Secretion | ± | − | − | + |
| Amount of Gastric Juice | + | − | − | + |

As shown above, DV-1006, unlike conventional anti-pepsin agents, exhibits a unique anti-pepsin action in inhibiting the secretion of pepsin.

Incidentally, it appears from the above table that anticholinergic agents produce similar results to those produced by DV-1006. However, DV-1006 does not cause any appreciable side-effects, which anticholinergic agents do involve frequently. That is, DV-1006 does not exhibit any inhibitory activity on carbachol stimulation in the Gosh and Schild method (see *Brit. J. Pharmacol*, 13 54 (1958)). Further, DV-1006 does not show general anticholinergic activities which typical anticholinergic agents possess. From a pharmacological standpoint, DV-1006 has the activity selectively inhibiting the secretion of pepsin without affecting acidity and the activity of pepsin itself.

It is also clear from the results of examinations using the above ulcer models that DV-1006 has the action of reducing the activity of mucopolysaccharase at the ulcer site which has been enhanced by the formation of the ulcer. The above two activities are new modes of action not observed in conventional agents on peptic ulcers.

From the results of the animal tests described above, it is appreciated that the compounds of the general formula (I) exhibit remarkable and unique activities as an anti-ulcer agent. Further, in order to confirm the anti-ulcer activities of the compounds of the general formula (I), clinical tests were also conducted using DV-1006 as a representative example of the compounds of the general formula (I). These clinical tests were performed on patients with gastric ulcers at National Zentsuji Hospital in Tokushima Prefecture, Japan. As a result, it was ascertained that DV-1006 exhibited a very marked curing effect on peptic ulcers when orally administered for several days at a dose of 300 to 1200 mg/day.

The compounds of the general formula (I) are known compounds, and are known to have an anti-plasmin activity. These compounds are stable and hardly have any toxicity. They can be prepared, for example, by the method disclosed in U.S. Pat. No. 3,699,149.

The compounds of this invention can be used in any desired formulation processed by conventional techniques, such as capsules, tablets, powders, injectable preparations or suppositories.

Depending upon the condition of the ulcer, the treating agent of this invention can be used together with other antiulcer agents such as anti-acid, or anti-pepsin agent or an anticholinergic agent, in which case a synergistic effect can be expected.

The dose of the treating agent of this invention varies according to the method of administration, but daily dosages per patient (about 60 kg body weight) of 300 to 1200 mg are sufficiently effective.

The following Examples are given to further illustrate the present invention in greater detail. Unless otherwise indicated all parts, percents, ratios and the like are by weight.

EXAMPLE 1

30 gastric ulcer patients at the Internal Treatment Department of National Zentsuji Hospital in Tokushima Prefecture, Japan, who had been so diagnosed by X-ray and endoscopes, were treated for 8 weeks using an oral administration of DV-1006 at a dosage of 200 mg three times per day. At the end of the 8-week period, 21 patients were completely cured (70%), the condition of 7 patients had been alleviated (23%). (No side-effects were observed in any of the patients).

EXAMPLE 2

Shay Ulcer Test

Donryu rats each weighing 200 to 240 g (six in each group) were starved for 48 hours, and ligated at a portion of the duodenum near the pylorus by the method of Shay et al (see *Gastroenterology*, 54, 43 (1945)). Immediately after the ligation, DV-1006 was orally administered to the rats at a dosage of 300 mg/Kg. After 18 hours, the abdomen of each of the rats was incised, and the stomach was removed. The results were evaluated by the method of Adami et al. (*Arch. Int. Pharmacodyn*, 147, 113 (1964)), and it was found that DV-1006 exhibited an inhibitory ratio of 100%.

In the same way as described above, gefarnate, a conventional anti-ulcer agent, was administered to the rats at a dosage of 100 mg/Kg. The gefarnate exhibited an inhibitory ratio of 83%.

EXAMPLE 3

Shay Ulcer Test by Intraperitoneal Administration

Some typical compounds of formula (I) were tested on Shay ulcers in the same way as described in Example 2 except that each of the compounds was suspended in a 0.5% aqueous solution of carboxymethyl cellulose and administered intraperitoneally. The results obtained are shown in Table 4 below. A statistical evaluation of the results showed that the anti-ulcer activities of the compounds of formula (I) were significantly different from the controls.

Table 4

| Q | Dosage (mg/Kg) | Ulcer Index | Inhibitory Ratio (%) |
|---|---|---|---|
| $(H_2NCH_2-\langle H \rangle \cdots COO \cdot Q)$ | | | |
| 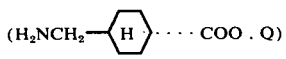 | 350 | 0.5±0.0 | 84 |
| Control | 0.5% CMC 1 ml/200 g | 3.2±0.2 | — |
| —CH$_2$CH$_2$COOH | 350 | 1.0±0.3 | 70 |
| 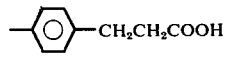—CH=CHCOOH | 350 | 0.8±0.3 | 76 |
| Control | 0.5% CMC 1 ml/200 g | 3.3±0.3 | — |
| 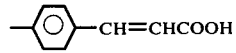—CHO (CH$_3$O) | 350 | 0.5±0.5 | 84 |
| 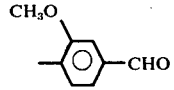 | 350 | 1.3±0.4 | 58 |
| 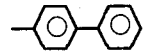 | 350 | 0.5±0.3 | 84 |
| Control | 0.5% CMC 1 ml/200 g | 3.1±0.3 | — |

Table 4-continued

| Q $(H_2NCH_2-\langle H \rangle \cdots COO \cdot Q)$ | Dosage (mg/Kg) | Ulcer Index | Inhibitory Ratio (%) |
| --- | --- | --- | --- |
| $-\langle O \rangle-COOH$ | 350 | 1.0±0.2 | 71 |
| $-\langle O \rangle-CH_2\underset{NH_2}{CH}COOH$ | 350 | 1.0±0.3 | 71 |
| Control | 0.5% CMC 1 ml/200 g | 3.4±0.4 | — |
| $-\langle O \rangle-Cl$ | 175 | 1.1±0.5 | 62 |
| Control | 0.5% CMC 1 ml/200 g | 2.9±0.5 | — |

EXAMPLE 4

Drug Ulcer Test

Female rats each weighing about 150 g (5 in each group) were starved for 20 hours, and then DV-1006 was administered to the rats. After one hour, 25 mg/Kg of indomethacin, 300 mg/Kg of aspirin and 200 mg/Kg of phenylbutazone, respectively, were administered orally to the rats and the rats were further starved for 5 hours. The stomach of each of the rats was removed, and the ulcer index was measured.

For comparison, the above procedure was repeated except that gefarnate and aluminum sucrose sulfate were used in their basic customary dosages.

The results obtained are shown in Table 5 below.

Table 5

| Drugs | Dosage (mg/Kg) (p.o.) | Inhibitory Ratio (%) | | |
| --- | --- | --- | --- | --- |
| | | Aspirin | Indomethacin | Phenyl-butazone |
| DV-1006 | 300 | 65.3 | 30.2 | 70.0 |
| Gefarnate | 100 | 42.8 | 29.0 | 31.5 |
| Aluminum sucrose sulfate | 1000 | 38.6 | 40.0 | 38.0 |

EXAMPLE 5

10% Acetic Acid Ulcer Test

Wistar rats, female and male, with a body weight of about 150 g were used (five in each group), and 0.05 ml of 10% acetic acid was injected into the submucosal layer of the anterior wall of the glandular stomach by the method of Takagi et al. (see *Japan J. Pharmacol.*, 19, 418 (1970)) to cause ulcers. Each of the drugs shown in FIG. 1 was orally administered to the rats once a day for 8 days starting on the date on which the acetic acid was injected. On the ninth day the rats were killed under ether anaesthesia. The stomach of each rat was removed, and opened along the greater curvature. The ulcer index was measured by means of slide calipers, and then the glandular stomach tissue was homogenized by adding a suitable amount of a physiological salt solution, and centrifuged for 20 minutes at a rate of 12,000 rpm. Using the supernatant liquid obtained, the activity of mucopolysaccharase was measured by the method of Hasebe et al (see Fukushima, *J. Med. Sci.*, 15, 35 (1968)).

The results obtained are shown in FIG. 1. DV-1006 exhibited a marked inhibitory action on the ulcers caused by acetic acid, as can be seen from the visual ulcer indices obtained. Moreover, DV-1006 showed a dose-response, and also reduced the activity of the mucopolysaccharase in the ulcer portion which is enhanced by the formation of ulcers.

EXAMPLE 6

Clamping Ulcer Test

Figure 2:
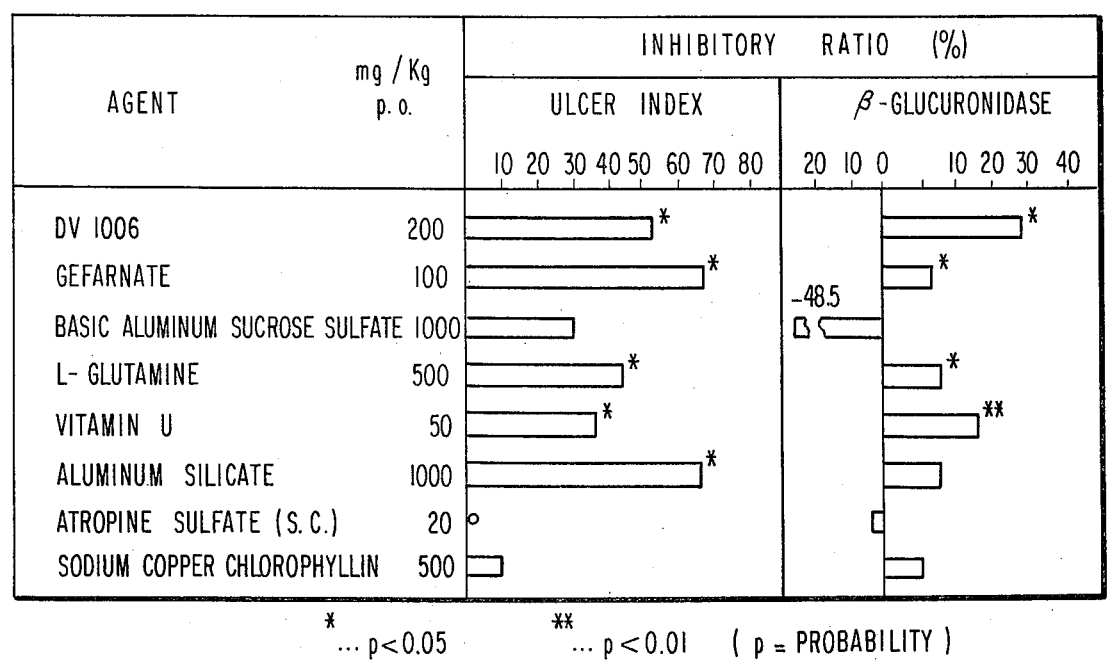
FIG. 2 shows the effect of 4'-(2-carboxyethyl)-phenyl.trans-4-aminomethylcyclohexane carboxylate and various known comparative ulcer treating agents on the ulcer index and β-glucuronidase activity in the glandular stomach tissue of rats with clamping ulcer 15 days after operation as described in the examples.

Clamping ulcers were formed by the method of Umehara et al (see *Peptic Ulcer*, Lippincott, Philadelphia (1971)) using Wistar male rats with a body weight of about 200 g (6 to 10 in each group). Each of the drugs shown in FIG. 2 was administered orally once in a day for 14 days starting on the day on which the aluminum metal plate was removed. On the fifteenth day, the rats were killed under ether anaesthesia, and the ulcer index and the mucopolysaccharase activity in the stomach tissue were measured. The results obtained are shown in FIG. 2. DV-1006 exhibited an especially significant inhibitory action on $\beta$-glucuronidase.

EXAMPLE 7

Clamping-Cortisone Ulcer Test

Ulcers were formed in rats in the same way as in Example 6. Then, 5 mg/Kg of hydrocortisone acetate was intramuscularly injected into the rats once a day for 7 days starting on the day on which the aluminum metal plate was removed. Each of the agents shown in FIG. 3 was administered orally to the rats once a day for 11 days starting on the day on which the administration of hydrocortisone acetate was stopped. On the twentieth day after the formation of the ulcers, the rats were killed under ether anaesthesia, and the ulcer index and the mucopolysaccharase activity were measured in the same way as in Example 6.

Figure 3:
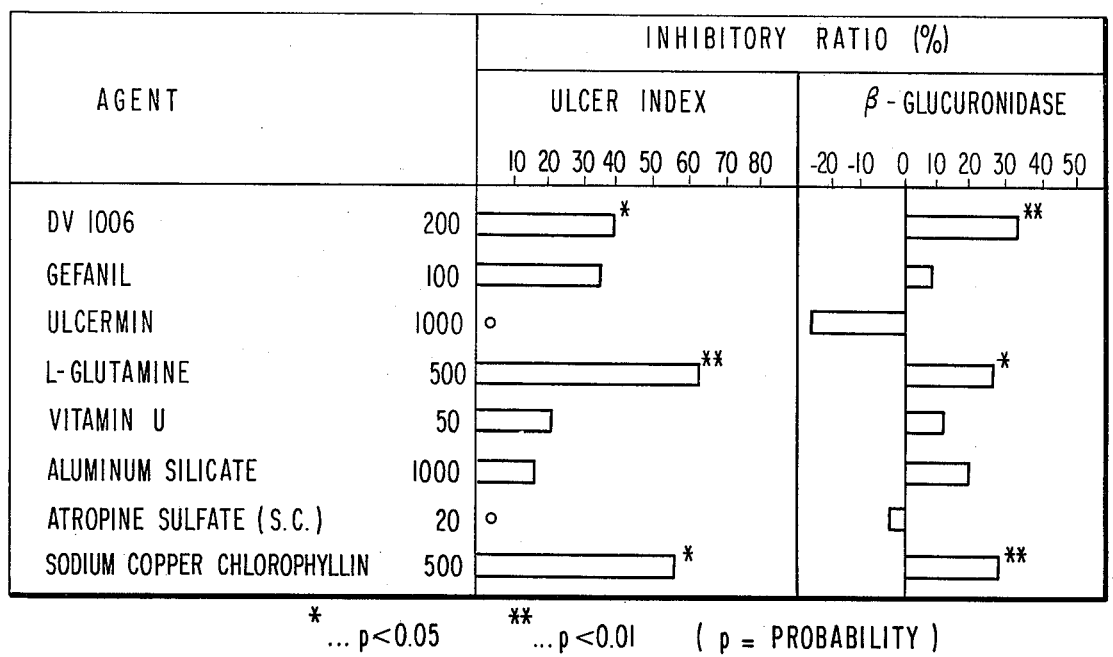
FIG. 3 shows the effect of 4'-(2-carboxyethyl)-phenyl.trans-4-aminomethylcyclohexane carboxylate and known comparative ulcer treating agents on the ulcer index and β-glucuronidase activity in glandular stomach tissue of rats with clamping-cortisone ulcer 20 days after operation as described in the examples.

The results obtained are shown in FIG. 3. DV-1006 exhibited an especially significant inhibitory action on the activity of $\beta$-glucuronidase.

EXAMPLE 8

Pepsin Secretion Inhibition Test (beef bouillon pot-au-feu soup stimulating test in Heidenhain pouch dogs)

After oral administration (first stimulation) of 70 ml of a mixture (100 ml) of 6 g of beef bouillon and 6 g of pot-au-feu soup, gastric juice was extracted every 15 minutes. When the secretion of gastric juice returned almost to the value before the stimulation, DV-1006 was orally administered at a dosage of 150 mg/Kg. The second stimulation was given 75 minutes later in the same way as in the first stimulation, and the amount of gastric juice secreted and the amount of pepsin secreted were measured [by the modified method of Anson-Maskey (see *J. Gen. Physiol.*, 16, 59 (1932))] with the passage of time.

Figure 4:
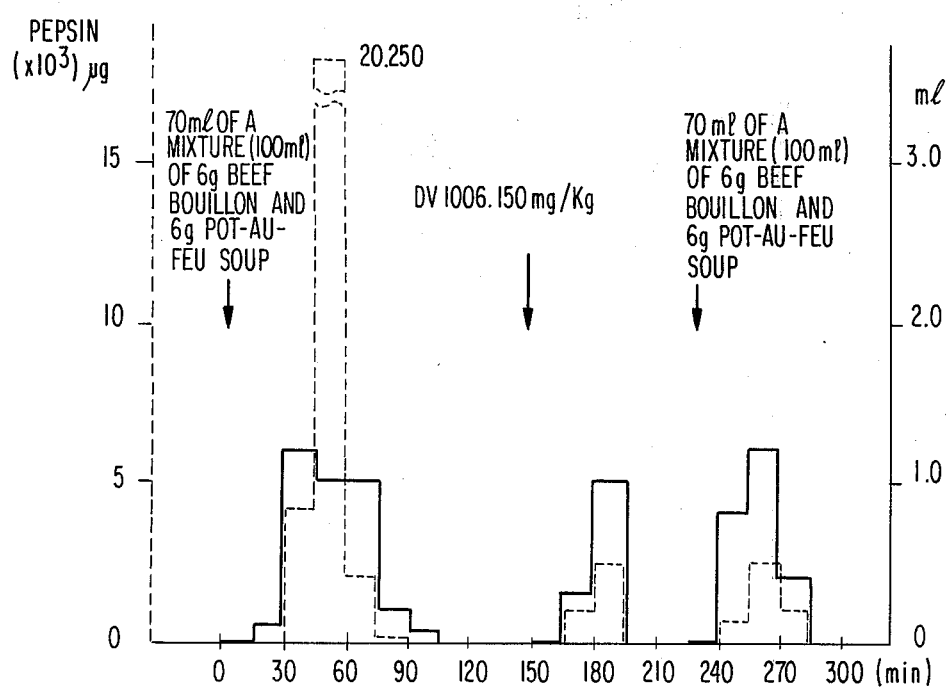
FIG. 4 shows graphically the results obtained on pepsin secretion inhibition in Heidenahin pouch dogs using 4'-(2-carboxyethyl)phenyl.trans-4-aminomethyl-cyclohexane carboxylate and comparative known ulcer treating agents as described in the examples.

The results obtained are shown in FIG. 4. It can be seen from the results in FIG. 4 that the administration of DV-1006 reduced both the amount of gastric juice and the amount of pepsin, and in particular, markedly inhibited pepsin secretion.

EXAMPLE 9

Capsule

Capsules were prepared according to the following formulation.

| | |
|---|---|
| DV-1006 | 100 mg (or 200 mg) |
| Microcrystalline Cellulose | 38 mg |
| Lactose | 40 mg |
| Magnesium Stearate | 2 mg |
| | 180 mg (per capsule) |

EXAMPLE 10

Tablets

Tablets were prepared according to the following formulation.

| | |
|---|---|
| DV-1006 | 100 mg (or 200 mg) |
| D-Mannitol | 50 mg |
| Polyvinyl Alcohol | 5 mg |
| Magnesium Stearate | 30 mg |
| | 185 mg (per tablet) |

EXAMPLE 11

Injectable Preparation

An injectable preparation was produced according to the following formulation.

| | |
|---|---|
| Lyophilized DV-1006 | 200 mg |
| Urea (as a dissolving assistant) | 500 mg |
| Acetic Acid buffer (pH=3.0) | 10 ml |

EXAMPLE 12

Suppository

A suppository was prepared according to the following formulation.

| | |
|---|---|
| DV-1006 | 100 mg (or 200 mg) |
| Glycerin Fatty Acid Ester | 800 mg |
| | 900 mg (per suppository) |

EXAMPLE 13

Powder

A powder was prepared according to the following formulation.

| | |
|---|---|
| DV-1006 | 200 mg |
| Lactose | 400 mg |
| Corn Starch | 380 mg |
| Hydroxypropyl Cellulose | 20 mg |
| | 1000 mg |

While the invention has been described in detail and with reference to specific embodiments thereof, it will be apparent to one skilled in the art that various changes and modifications can be made therein without departing from the spirit and scope thereof.

What is claimed is:

1. A method for treating peptic ulcers in a patient in need of said treatment comprising administering to said patient a therapeutically effective amount of an amino acid ester of the general formula (I)

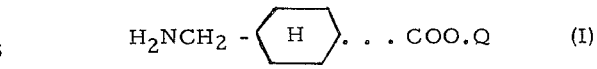

wherein Q is an unsubstituted or substituted phenyl or β-naphthyl group, the substituted phenyl group being selected from the group consisting of a p-chlorophenyl group, an o-methoxy-p-formylphenyl group, a diphenyl group, a p-carboxyvinylphenyl group, a p-carboxyphenyl group, and a p-carboxy-lower alkyl phenyl group.

2. The method of treating peptic ulcers of claim 1, wherein said amino acid ester of the general formula (I) is 4'-(2-carboxyethyl)phenyl.trans-4-aminomethyl cyclohexane carboxylate.

3. The method for treating peptic ulcers of claim 1, comprising administering the amino acid ester of the general formula (I) at a dosage of 300 to 1200 mg/day/60 kg of body weight.

4. The method for treating peptic ulcers of claim 2, comprising administering 4'-(2-carboxyethyl)phenyl.-trans-4-aminomethyl cyclohexane carboxylate at a dosage of 300 to 1200 mg/day/60 kg of body weight.

5. The method of treating peptic ulcers of claim 1, comprising administering the amino acid ester of the general formula (I) with a pharmaceutically acceptable excipient.

6. The method of treating peptic ulcers of claim 1, comprising administering 4'-(2-carboxyethyl)phenyl.-trans-4-aminomethyl cyclohexane carboxylate, with a pharmaceutically acceptable excipient.

* * * * *